United States Patent
Raveendranath et al.

(10) Patent No.: US 6,169,082 B1
(45) Date of Patent: Jan. 2, 2001

(54) SALTS OF 8,9-DEHYDROESTRONE SULFATE ESTER

(75) Inventors: Panolil C. Raveendranath, Plattsburgh, NY (US); John A. Wichtowski, Middletown, CT (US)

(73) Assignee: American Home Products Corporation, Madison, NJ (US)

(*) Notice: Under 35 U.S.C. 154(b), the term of this patent shall be extended for 0 days.

(21) Appl. No.: 08/019,387

(22) Filed: Feb. 18, 1993

Related U.S. Application Data

(63) Continuation-in-part of application No. 07/841,694, filed on Feb. 26, 1992, now Pat. No. 5,210,081.

(51) Int. Cl.[7] .............................. A61K 31/56; C07J 1/00
(52) U.S. Cl. .................... 514/179; 552/625; 552/626
(58) Field of Search ..................................... 552/503, 625, 552/626; 514/179

(56) References Cited

U.S. PATENT DOCUMENTS

| | | |
|---|---|---|
| 2,834,712 | 5/1958 | Beall et al. . |
| 3,391,169 * | 7/1968 | Hughes et al. .................. 260/397.45 |
| 3,394,153 | 7/1968 | Re . |
| 3,608,077 | 9/1971 | Glasig . |
| 3,649,621 | 3/1972 | Stein et al. . |
| 4,154,820 | 5/1979 | Simoons . |
| 5,210,081 * | 5/1993 | Raveendranath et al. ........... 514/179 |
| 5,288,717 * | 2/1994 | Raveendranath et al. ........... 514/179 |

\* cited by examiner

*Primary Examiner*—Barbara Badio
(74) *Attorney, Agent, or Firm*—Arnold S. Milowsky

(57) ABSTRACT

This invention presents alkali metal salts of 8,9-dehydroestrone, salts of its sulfate ester, and stable compositions thereof, as well as processes for their production and use in estrogen replacement therapy and cardiovascular protection.

12 Claims, No Drawings

SALTS OF 8,9-DEHYDROESTRONE SULFATE ESTER

RELATED APPLICATIONS

This is a continuation-in-part of U.S. patent application Ser. No. 07/841,694 filed Feb. 26, 1992 by Panolil C. Raveendranath and John A Wichtowski, now U.S. Pat. No. 5,210,081.

BACKGROUND OF THE INVENTION

The use of naturally occurring estrogenic compositions of substantial purity and low toxicity such as Premarin® has become a preferred medical treatment for alleviating the symptoms of menopausal syndrome, osteoporosis/ osteopenia in estrogen deficient women and in other hormone related disorders. The estrogenic components of the naturally occurring estrogenic compositions have been generally identified as sulfate esters of estrone, equilin, equilenin, β-estradiol, dihydroequilenin and β-dihydroequilenin (U.S. Pat. No. 2,834,712). The estrogenic compositions are usually buffered or stabilized with alkali metal salts of organic or inorganic acids at a substantially neutral pH of about 6.5 to 7.5. Urea has also been used as a stabilizer (U.S. Pat. No. 3,608,077). The incorporation of antioxidants to stabilize synthetic conjugated estrogens and the failure of pH control with Tris® to prevent hydrolysis is discussed in U.S. Pat. No. 4,154,820.

8,9-Dehydroestrone is a known compound useful as an intermediate in the synthetic production of estrone by isomerization to 9,11 unsaturation (U.S. Pat. No. 3,394,153) and as an intermediate in the production of 3-cyclopentyloxy-17-ethynyl derivatives (Example XXVIII, U.S. Pat. No. 3,649,621). In addition, 8,9-dehydroestrone is known to possess estrogenic activity and to lower blood lipid levels (Examples 11 and 12; U.S. Pat. No. 3,391,169).

DESCRIPTION OF THE INVENTION

In accordance with this invention there is provided a group of pharmaceutically acceptable salts of 8,9-dehydroestrone sulfate ester. The pharmaceutically acceptable salts of this invention are the alkali metal, alkaline earth metal, ammonium, alkylamine and dialkylamine salts of 8,9-dehydroestrone sulfate ester. The alkali metal salts are those which are free from other conjugated esters present in material found in natural sources of mixed esters. In addition, stabilized salts of 8,9-dehydroestrone sulfate ester in combination with tris(hydroxymethyl)aminomethane are provided, as well as the use of the 8,9-dehydroestrone-3-sulfate ester salts and 8,9-dehydroestrone itself in the treatment of cardiovascular diseases.

Furthermore, a process for the production of salts of 8,9-dehydroestrone sulfate esters and their stabilized compositions is provided which affords excellent product control. The process of this invention differs from methods generally involved in the sulfation of steroids which are carried out by treatment of the steroid with amine-sulfurtrioxide complexes followed by treatment with a cation exchange resin mediated by strong alkaline bases, preferably in hydroxylic solvents. Those reported methods for sulfation of steroids proved ineffective in the sulfation of 8,9-dehydroestrone. The process disclosed here relies upon the initial production of an alkali metal salt of 8,9-dehydroestrone followed by sulfation with trimethylamine-sulfurtrioxide under mild conditions in a polar, aprotic solvent such as tetrahydrofuran with simultaneous or subsequent addition of tris (hydroxymethyl)aminomethane as a stabilizer. The alkaline bases employed in the production of the initial intermediates of 8,9-dehydroestrone are preferably sodium or potassium in the form of their hydrides and lithium as n-butyllithium.

The alkaline earth metal salts containing the calcium or magnesium cation are produced with the appropriate base by transmetalation of the alkali metal salt directly or via exchange with a cation exchange resin such as the weakly acidic Amberlite exchangers DP-1, IRC-50, IRC-76, CG-50 or IRP-64, on the appropriate cycle. Acidification of the alkali metal salt of the sulfate esters with a mild acid such as acetic acid, followed by extraction with an alcohol such as n-butanol and neutralization with a stoichiometric amount of calcium or magnesium hydroxide, ammonium hydroxide or the desired amine affords the other salts when desired. In the case of the amine salts, the mono-alkylamines contain from 1 to 6 carbon atoms, such as methylamine, ethylamine, propylamine, isopropylamine, butylamine, tertiary butylamine, hexylamine, and the like. The dialkylamine salts contain from 1 to 6 carbon atoms in each alkyl group and are produced from dimethylamine, diethylamine, diisopropylamine, di(2-methylpentyl)amine, dihexylamine, and the like.

The following examples illustrate the preparation of the salts of 8,9-dehydroestrone by direct metallation with NaH, KH or n-butyl lithium in tetrahydrofuran under an inert atmosphere at about 0° C. The alkali metal salt containing solution is used directly in the sulfation reaction. The introduction of tris(hydroxymethyl)aminomethane at various stages of the process is also illustrated. Examples 6 and 7 illustrate the stabilizing influence of tris(hydroxymethyl) aminomethane.

EXAMPLE 1

Sodium 8,9-dehydroestrone-3-sulfate

To a stirred suspension of sodium hydride (0.24 g, 10 mmol) in tetrahydrofuran (20 mL), at 0° C., under nitrogen, was added a solution of 8,9-dehydroestrone (2.68 g, 10 mmol) in tetrahydrofuran (30 mL). After 10 minutes, the cooling bath was removed to allow the reaction mixture to attain room temperature. To this was added trimethylamine-sulfurtrioxide complex (1.39 g, 10 mmol). After stirring for 10 minutes, tris(hydroxymethyl)aminomethane (1.79 g, 15 mmol) was added and stirring continued overnight. The solvent was evaporated off and the residue taken up in water (180 mL) and washed with diethyl ether (2×50 mL). The aqueous solution was filtered using a sintered glass funnel (medium porosity) and the filtrate subjected to lyophilization to obtain 5.2 g of solid material.

Analysis Profile

HPLC purity of sodium 8,9-dehydroestrone-3-sulfate—96.3%.

Acidification of an aqueous solution of sodium 8,9-dehydroestrone-3-sulfate to obtain the free sulfate ester followed by extraction with n-butanol and neutralization of the acid with calcium hydroxide and lyophilization of the product affords calcium 8,9-dehydroestrone-3-sulfate. The analogous reaction with magnesium hydroxide or ammonium hydroxide affords magnesium 8,9-dehydroestrone-3-sulfate and ammonium 8,9-dehydroestrone-3-sulfate, respectively.

EXAMPLE 2

Sodium 8.9-dehydroestrone-3-sulfate

To a stirred suspension of sodium hydride (0.24 g, 10 mmol) in tetrahydrofuran (20 mL), at 0° C., under nitrogen, was added a solution of 8,9-dehydroestrone (2.68 g, 10 mmol) in tetrahydrofuran (30 mL). After stirring for 30 minutes at room temperature, tris(hydroxymethyl) aminomethane (1.79 g, 10 mmol) was added and after another 30 minutes trimethylamine-sulfurtrioxide complex (1.39 g, 10 mmol) was added and the solution was stirred overnight. The solvent was removed evaporatively and the residue was taken up in water (40 mL). The aqueous layer was washed with diethyl ether (2×20 mL) and then lyophilized to afford 5.1 g of solid material.

Analytical Profile

HPLC purity of sodium 8,9-dehydroestrone-3-sulfate—96.2%.

An aqueous solution of sodium 8,9-dehydroestrone-3-sulfate is passed through a column of Amberlite IRC-50 to obtain the free sulfate ester as the acid, which is treated with ethylamine to obtain the ethylamine salt of 8,9-dehydroestrone-3-sulfate by lyophilization of the product. With dimethylamine, the dimethylamine 8,9-dehydroestrone-3-sulfate salt is obtained.

EXAMPLE 3

Sodium 8.9-dehydroestrone-3-sulfate

To a stirred suspension of sodium hydride (0.24 g, 10 mmol) in tetrahydrofuran (20 mL), at 0° C., under nitrogen, was added a solution of 8,9-dehydroestrone (2.68 g, 10 mmol) in tetrahydrofuran (30 mL). After letting the reaction mixture warm to room temperature, it was stirred for 30 minutes and trimethylamine-sulfurtrioxide complex (1.39 g, 10 mmol) was added. Stirring continued overnight. Solvents were evaporated off and the residue taken up in water (50 mL), the aqueous layer was washed with diethyl ether (2×20 mL) and tris(hydroxmethyl)-aminomethane (1.21 g, 10 mmol) was added. The resulting clear solution was lyophilized to obtain 5.04 g of solid material.

Analytical Profile

HPLC purity of sodium-8,9-dehydroestrone-3-sulfate—96.2%.

EXAMPLE 4

Lithium 8.9-dehydroestrone-3-sulfate

To a mixture of tris(hydroxmethyl)aminomethane (0.63 g, 5.2 mmol) and 8,9-dehydroestrone (0.94 g, 35 mmol) in the tetrahydrofuran (14 mL), at −70° C., under nitrogen, was added n-butyl lithium (2.5 M solution in hexanes, 1.4 mL). After stirring at this temperature for 10 minutes, the cooling bath was removed. At 0° C., was added trimethylamine-sulfurtrioxide complex (0.49 g, 3.5 mmol), allowed to reach ambient temperature and continued stirring overnight. Solvents were evaporated off and the residue taken up in water (150 mL). This aqueous solution was washed with diethyl ether (3×35 mL) and lyophilized to afford 1.11 g of solid material.

Analytical Profile

HPLC purity of lithium 8,9-dehydroestrone-3-sulfate—90.4%.

EXAMPLE 5

Potassium 8.9-dehydroestrone-3-sulfate

To a stirred suspension of potassium hydride (0.14 g, 3.5 mmol) in tetrahydrofuran (14 mL) at 0° C., under nitrogen, was added tris-(hydroxymethyl)aminomethane (0.63 g, 5.2 mmol), followed by a solution of 8,9-dehydroestrone (0.94 g, 3.5 mmol) in tetrahydrofuran (14 mL). After 15 minutes trimethylamine-sulfurtrioxide complex (0.48 g, 3.5 mmol) was added. After letting the reaction mixture reach room temperature, an additional quantity of tetrahydrofuran (15 mL) was added and stirring was continued overnight. Solvents were evaporated off and the residue was taken up in water (150 mL). This aqueous solution was washed with diethyl ether (3×35 mL) and subsequently lyophilized to obtain 1.63 g of solid material.

Analytical Profile

HPLC purity of potassium 8,9-dehydroestrone-3-sulfate—91.3%.

An aqueous solution of potassium 8,9-dehydroestrone-3-sulfate is passed through an ion exchange column containing Amberlite IRP-64 employing a strong calcium hydroxide solution as the eluant to obtain calcium 8,9-dehydroestrone-3-sulfate. The magnesium and ammonium salts are obtained in the same manner.

From these procedures it can be seen that the process of this invention proceeds smoothly to provide highly pure product.

EXAMPLE 6

Sodium 8.9-dehydroestrone-3-sulfate

To a stirred suspension of NaH (0.57 g, 24 mmol) in tetrahydrofuran (50 mL) at 0° C., under nitrogen, was added a solution of 8,9-dehydroestrone (5.36 g, 20 mmol) in tetrahydrofuran (100 mL), over a period of 10 minutes. The reaction mixture was allowed to warm to room temperature and trimethylamine-sulfurtrioxide complex (3.34 g, 24 mmol). Stirring continued for 24 hours. Solvent was removed and dry solids resuspended in diethyl ether and extracted with water (100 mL). The aqueous layer was separated, washed with diethyl ether (2×20 mL) and lyophilized to afford 5.65 g of solid material.

Analytical Profile

HPLC strength of sodium 8,9-dehydroestrone-3-monosulfate—73.8%.

HPLC strength of sodium 8,9-dehydroestrone-3-monosulfate—33% (retested after two weeks).

EXAMPLE 7

Sodium 8.9-dehydroestrone-3-sulfate

To a stirred suspension of sodium hydride (0.72 g, 30 mmol) in tetrayhydrofuran (50 mL) was added at 0° C., under nitrogen, tris(hydroxymethyl)-aminomethane (5.38 g, 44 mmol) followed by a solution 8,9-dehydroestrone (8.04 g, 30 mmol) in tetrahydrofuran (110 mL). After allowing the reaction mixture to reach room temperature, trimethylamine-sulfurtrioxide (4.21 g, 30 mmol) was added and stirred for 24 hours. The reaction mixture was worked up as in Example 6 to afford 15.2 g of solid material.

Analytical Profile

HPLC/GC strength of sodium-8,9-dehydroestrone-3-monosulfate—55.8%.

HPLC strength of sodium-8,9-dehydroestrone-3-monosulfate—55.3% (retested after two weeks).

HPLC strength of tris(hydroxylamine)aminomethane—30.9%.

Spectral Characterization $^1$H and $^{13}$CNMR (400 MHz)—consistent.

$^1$H NMR also indicates that the ratio of conjugated estrogen to tris-(hydroxymethyl)aminomethane is about 1:1.5.

From Example 6, it is seen that in the absence of stabilization, the sulfate ester rapidly degrades while tris (hydroxymethyl)aminomethane provides protection from hydrolytic degradation as shown in Example 7 where the strength of the sulfate ester remained substantially constant over a two week period, thereby demonstrating better product control than obtained in the absence of tris (hydroxymethyl)aminomethane. The stabilized product is isolated in solid state, in a high state of purity and possesses desired water solubility properties at or near a neutral pH in conjunction with its pharmaceutical estrogenic activity.

The estrogenic activity of the compounds of this invention was established by administering them either orally or parenterally (subcutaneously) to rats and mice over a 7 day and 3 day period, respectively, and measuring the uterine weight gain in comparison with vehicle control. The results of these standard experimental procedures were as follows.

TABLE I

Estrogenicity of Sodium 8,9-Dehydroestrone-3-Sulfate - Rat Uterine Weight

| Treatment[a] | Dose[b] ($\mu$g) | Route | Wt. (mg) |
|---|---|---|---|
| Vehicle (oil) | — | s.c. | 46.3 ± 2.7 |
| Vehicle (dH$_2$O) | — | s.c. | 43.4 ± 3.5 |
| Sodium 8,9-dehydroestrone-3-sulfate | 0.1 | s.c. | 39.8 ± 2.1 |
| | 0.3 | s.c. | 46.1 ± 2.4 |
| | 1.0 | s.c. | 50.3 ± 2.7 |
| | 3.0 | s.c. | 71.9 ± 1.2 |
| | 10.0 | s.c. | 92.2 ± 5.7 |

[a]Six rats per group
[b]Daily dose over 7 days

TABLE II

Estrogenicity of Sodium 8,9-Dehydroestrone-3-Sulfate - Mouse Uterine Weight

| Treatment[a] | Dose[b] ($\mu$g) | Route | Wt. (mg) |
|---|---|---|---|
| Vehicle (dH$_2$O) | 0.3ml | s.c. | 11.2 ± 0.3 |
| Sodium 8,9-dehydroestrone-3-sulfate | 0.1 | s.c. | 17.9 ± 3.0 |
| | 0.3 | s.c. | 18.9 ± 2.3 |
| | 1.0 | s.c. | 21.3 ± 2.6 |
| | 3.0 | s.c. | 23.1 ± 3.2 |
| | 10.0 | s.c. | 22.7 ± 0.8 |
| Sodium 8,9-dehydroestrone-3-sulfate | 0.3 | p.o. | 18.4 ± 1.4 |
| | 1.0 | p.o. | 14.6 ± 1.7 |
| | 3.0 | p.o. | 17.8 ± 0.4 |
| | 10.0 | p.o. | 19.1 ± 0.9 |
| | 30.0 | p.o. | 24.1 ± 1.1 |

[a]Four mice per group
[b]Total dose over 3 days

Thus, the salts of 8,9-dehydroestrone-3-sulfate esters of this invention are estrogens useful in replacement therapy in estrogen deficiency. Further, they are useful in suppression of lactation, prophylaxis and treatment of mumps orchitis and senile osteoporosis. For veterinary purposes, the steroids of this invention are useful in replacement therapy for underdeveloped females, incontinence, vaginitis of spayed bitches, in uterine inertia, pyometra and in retained fetal membranes. In addition, the compounds of this invention are of especial interest in that they possess cardiovascular protective properties and they are useful in the treatment of atherosclerosis. These cardiovascular protective properties are of great importance when treating postmenopausal patients with estrogens to prevent osteoporosis and in the male when estrogen therapy is indicated.

The treatment of atherosclerosis is generally directed toward attenuation of sequelae (angina pectoris, myocardial infarction, arrhythmias, heart failure, kidney failure, stroke, peripheral arterial occlusion, and related disease states) with administration of antilipidemic drugs, reduction of blood pressure by 10 to 20% and increasing high density lipid blood levels by diet and exercise. These measures are generally designed to slow the rate of progress of the disease state rather than reverse its direction. Anti-athersclerotic agents are frequently administered in conjunction with other medicaments commonly employed in the treatment of that disease state, such as antilipidemic agents, antiarrhythmic agents, beta-blockers, and the like. Hence, the blood lipid lowering properties of the compounds of this invention provide an additional advantage to their use in the treatment of athersclerosis.

In accordance with the cardiovascular protective element of this invention, there is provided a process for treating atherosclerosis which comprises administering, orally or parenterally, an anti-atherosclerosis amount of an alkali metal , alkaline earth metal ammonium, alkylamine or dialkylamine salt of 8,9-dehydroestrone-3-sulfate ester in which the alkyl groups of the amine salts contain from 1 to 6 carbon atoms. Of course, 8,9-dehydroestrone itself, the putative metabolite or in vivo hydrolysis product of the sulfate ester salts exhibits the same cardiovascular protective influence as the ester salts and may be employed directly by itself if it is available and its use feasible in a given situation. Both arterial surface area lesions and arterial cholesterol content can be reduced significantly in a dose related manner by this steroid.

When the steroids of this invention are employed as estrogenic agents or as unique cardiovascular protective agents in warm-blooded animals, they may be administered alone or in combination with pharmacologically acceptable carriers, the proportion of which is determined by the solubility and chemical nature of the compound, chosen route of administration and standard pharmacological practice. For example, they may be administered orally in the form of tablets or capsules containing such excipients as starch, milk, sugar, certain types of clay, and so forth. They may also be administered orally in the form of solutions which may contain coloring and flavoring agents or they may be injected parenterally. For parenteral administration, they may be used in the form of a sterile solution containing other solutes; for example, enough saline or glucose to make the solution isotonic.

The dosage of the present therapeutic agents will vary with the form of administration and the particular compound chosen. Furthermore, it will vary with the particular subject under treatment. Generally, treatment is indicated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in the range of from about 0.02 mcgm. to about 500 mcgm. per kilo per day, although as aforementioned variations will occur based upon the age, sex, body weight, severity of the disease state, prophylactic regimen, etc. In any event,the close observation and follow-up by the attending physician is necessary to achieve a desired therapeutic response in a given patient.

What is claimed is:

1. A pharmaceutically acceptable alkaline earth metal, ammonium or amine salt of 8,9-dehydroestrone-3-sulfate ester free from other estrogenic steroids, wherein the amine of said salt is selected from the group consisting of an alkylamine of 1 to 6 carbon atoms and a dialkylamine in which each alkyl group has, independently, 1 to 6 carbon atoms.

2. A compound of claim 1 which is calcium 8,9-dehydroestrone-3-sulfate.

3. A compound of claim 1 which is magnesium 8,9-dehydroestrone-3-sulfate.

4. A compound of claim 1 which is ammonium 8,9-dehydroestrone-3-sulfate.

5. A compound of claim 1 which is an alkylamine salt of 8,9-dehydroestrone-3-sulfate in which the alkyl moiety of the amine contains 1 to 6 carbon atoms.

6. A compound of claim 5 which is the ethylamine salt of 8,9-dehydroestrone-3-sulfate.

7. A compound of claim 1 which is a dialkylamine salt of 8,9-dehydroestrone-3-sulfate in which each of the alkyl moieties of the amine contain 1 to 6 carbon atoms.

8. A compound of claim 7 which is the dimethylamine salt of 8,9-dehydroestrone-3-sulfate.

9. A method for the treatment of atherosclerosis which comprises administering to a patient in need of anti-atherosclerotic treatment, an effective amount of a salt of 8,9-dehydroestrone sulfate ester.

10. A method of claim 9 in which said salt of 8,9-dehydroestrone sulfate ester is the calcium, magnesium, ammonium, alkylamine or dialkylamine salt in which each of the alkyl groups of said amines contain from 1 to 6 carbon atoms.

11. A method of removing arterial lesions attending the development of atherosclerosis which comprises administering, orally, or parenterally, to a patient suffering from atherosclerosis, a pharmaceutical composition containing an anti-atherosclerotic amount of a salt of 8,9-dehydroestrone sulfate ester.

12. A method of claim 11 in which said salt of 8,9-dehydroestrone sulfate ester is the calcium, magnesium, ammonium, alkylamine or dialkylamine salt in which each of the alkyl groups of said amines contain from 1 to 6 carbon atoms.

* * * * *